United States Patent

Eggers et al.

Patent Number: 5,855,786
Date of Patent: Jan. 5, 1999

[54] PROCESS FOR HIGH-PRESSURE SPRAY EXTRACTION OF LIQUIDS

[76] Inventors: Rudolf Eggers, Stader Strasse 68, D-21614 Buxtehude, Germany; Henning Wagner, Baanstraat 17, NL-3111 KM Schiedam, Netherlands; Michael Schneider, Ausschläger Elbdeich 62, D-20539 Hamburg, Germany

[21] Appl. No.: 817,234
[22] PCT Filed: Oct. 6, 1995
[86] PCT No.: PCT/EP95/03950
  § 371 Date: Apr. 10, 1997
  § 102(e) Date: Apr. 10, 1997
[87] PCT Pub. No.: WO96/11043
  PCT Pub. Date: Apr. 18, 1996

[30] Foreign Application Priority Data

Oct. 11, 1994 [DE] Germany .......................... 44 36 223.4

[51] Int. Cl.⁶ .................................................. B01D 11/04
[52] U.S. Cl. ................................................... 210/634
[58] Field of Search ................................. 210/634, 639; 426/417, 427

[56] References Cited

U.S. PATENT DOCUMENTS

| | | | |
|---|---|---|---|
| 4,367,178 | 1/1983 | Heigel | 260/403 |
| 4,812,233 | 3/1989 | Coenen | 210/177 |
| 4,828,702 | 5/1989 | Coenen | 210/634 |
| 5,229,000 | 7/1993 | Ben-Nasr | 210/634 |
| 5,258,057 | 11/1993 | Baykut | 95/89 |
| 5,288,511 | 2/1994 | Kazlas | 426/427 |

FOREIGN PATENT DOCUMENTS

| | | | |
|---|---|---|---|
| 0137214 | 4/1985 | European Pat. Off. | 210/634 |
| 0450378 | 10/1991 | European Pat. Off. | 210/634 |
| 0464968 | 1/1992 | European Pat. Off. | 210/634 |
| 3919384 | 12/1990 | Germany | 210/634 |

*Primary Examiner*—Ernest G. Therkorn
*Attorney, Agent, or Firm*—Lane, Aitken & McCann

[57] ABSTRACT

A liquid high pressure splaying extraction process by means of compressed gas is disclosed. A liquid and gas are mixed in a mixing zone and substances contained in the spray particles that leave the mixing zone are separated in a separate loading zone, where spray particles are able to dwell for a sufficient period of time. Geometrically optimized flight paths for substance transfer are provided.

7 Claims, 4 Drawing Sheets

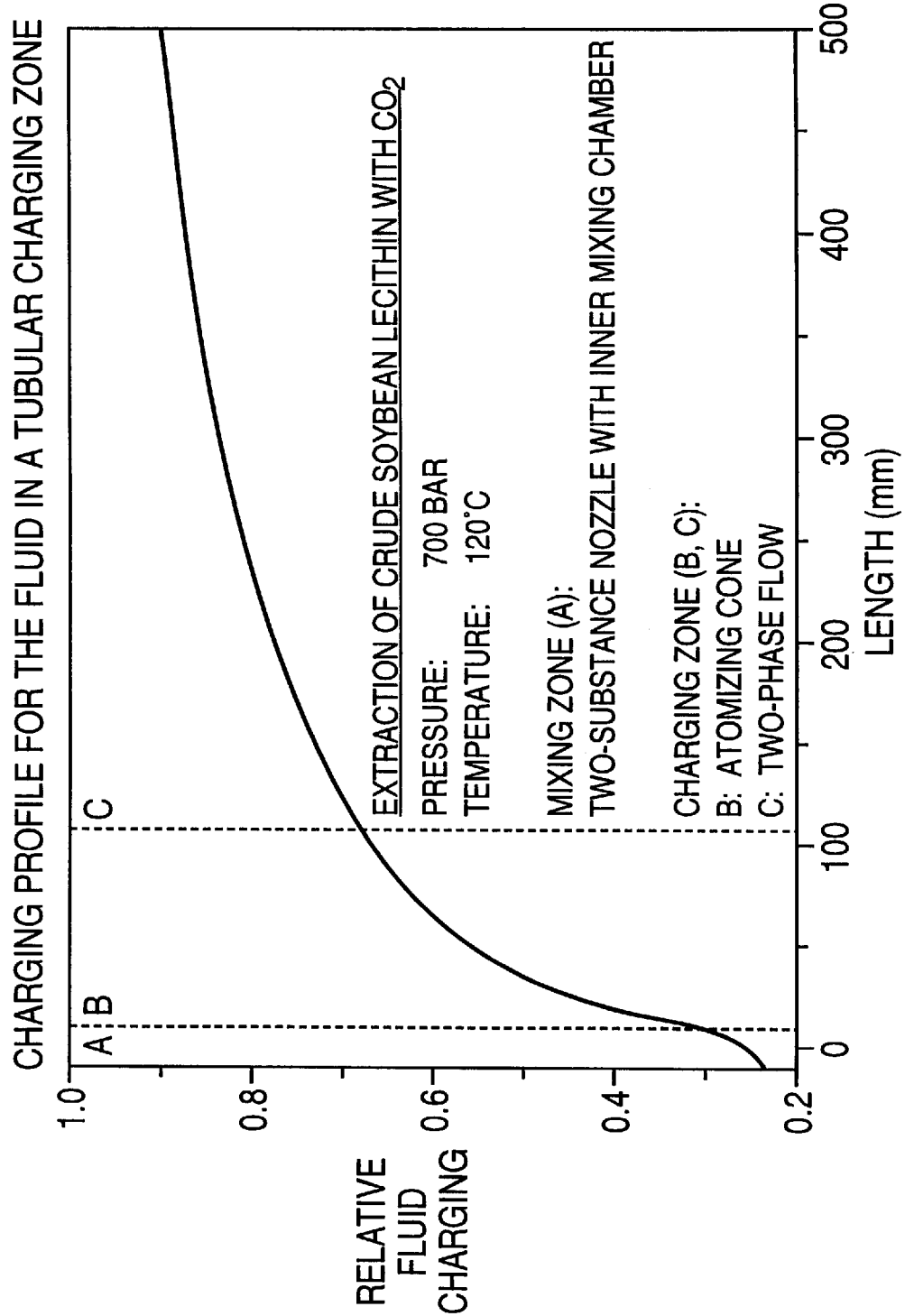

PROCESS FOR HIGH-PRESSURE SPRAY EXTRACTION OF LIQUIDS

REFERENCE TO RELATED APPLICATIONS

This application is a 371 of PCT/EP95/03950 filed Oct. 6, 1995.

The invention relates to a process for high-pressure spray extraction of liquid solutions and suspensions in the pressure range up to 1,000 bar by means of compressed gases such as $CO_2$, propane, butane and mixtures thereof with and without entrainer additives such as: ethanol, propanol, methanol, acetone, water, methyl-ethyl-ketone, comprising liquid and gas mixing and mass transfer.

As is well known, the setting of an optimal dwell time is necessary for extraction processes. In discontinuous batch processes, this is produced by the period of extraction gas impact (DE 33 16 705 A1). As opposed to this, the process according to the invention allows the continuous guiding of the extraction gas while at the same time ensuring optimal dwell times for the liquid in this gas.

The use of alternating pressure impact for reducing the size of solids is known (DE 26 32 045 C2). With extraction procedures with compressed gases, however, the dispersion of a liquid must take place with as little pressure loss as possible because otherwise, the solubility of the gas decreases considerably and extraction becomes impossible. An alternating pressure impact would also be disadvantageous because the attainable drop ranges would then no longer be constant in time and product quality would thus be nonuniform. The technical problem of the invention is therefore to indicate a high-pressure spray extraction process in which a constant fine-dispersion of the liquid is achieved in a spraying device without alternating pressure impact and the optimal dwell time is set in an appropriate extraction geometry.

Unlike known nozzle extraction processes, in high-pressure spray extraction the charging does not take place in a mixing chamber, rather a distinction is made between a mixing zone and a charging zone adjoining it.

The spatial separation of the two process steps "mixing" and "charging" is advantageous physically speaking, because with a variable design of these two zones according to the invention a) during mixing, a substantially increased turbulence or finer drop formation can be set compared to known devices and b) in the subsequent charging zone, the spray particles emerging from the mixing zone can be given an adequate dwell time and geometrically optimized flight trajectories for the mass transfer (charging).

Compared to conventional spraying processes, high-pressure spray extraction offers the advantage that the prevailing process conditions have a positive effect on the spraying. The solubility of the gas in the liquid, substantially increased under pressure, leads to a considerable reduction in viscosity, in such a way that the liquid can be more easily dispersed into drops. But particularly the reduction of the interfacial tension between the phases to be mixed, noted as pressure increases, causes small drops to form (documentation: computer-assisted photographic image of two drops in supercritical carbon dioxide under different levels of pressure).

Furthermore, the mixing zone should be geometrically designed in such a way that due to an optimal pulse exchange, the high kinetic energy of the compressed gas is utilized to disperse the liquid into small drops. The spatial layout of the mixing zone for the spray extraction can be implemented as a two-substance nozzle with high-turbulent cross-flow or swirling flow of the gas as well as two single-substance nozzles (impact effect) directed toward each other. The use of a static mixer with subsequent unitary atomization of the gas and liquid is also conceivable.

The design of the charging zone is determined by the dwell time necessary for the mass transfer. A cylindrical design is sensible for relatively brief dwell times, e.g. for removing the oil from crude lecithin, because the mass transfer is completed before the sprayed particles hit the wall of the charging zone. There are greater transfer resistances for aqueous phases, such that the charging zone must allow longer dwell times without wall contact, e.g. a spherical or cut-off cone shape is advantageous for the separation of caffeine or nicotine from aqueous solutions. The same is true when the absorbing phase must be charged with nearly the entire feed stream, e.g. with crude oil desliming, in which approx. 98% of the feed stream goes into solution and the phosphatides are separated in the charging zone.

Along with the extraction, a certain particle formation can also be strived for. For this, it is sensible to present a different gas in the extraction zone than the one used for the extraction. The gas mixture forming is then marked by a modified solution quality, in such a way that the desired substances turn out as microcrystalline particles (example: extraction with $CO_2$ in an extraction zone with $N_2$).

Application of the process according to the invention

The high-pressure spray extraction with separate mixing and charging zone is suitable for genuine separation problems such as:

removing the oil from crude lecithin desliming of crude oil removing the oil from hydrolyzed soybean lecithin removing the fat and removing the cholesterol from liquid eggs lipid extraction from biomasses from fermentation extraction of distilled oils and aromas from aqueous or alcoholic plant extracts removal of active ingredients from aqueous solutions caffeine from coffee or tea extracts, ginseng, pesticide removal from aqueous or oily plant extracts (e.g. hop)

extraction of microcrystalline substances, e.g. medicines for inhalers) from solutions, whereby the solvent is soluble in compressed gas (mixture) (e.g. ethanol, water, among other things)

drying of aqueous solvent-containing mixtures.

It is also suitable for the production of new products, e.g. for coating antibiotics with phospholipids that were dissolved together beforehand, e.g. in an alcohol mixture that changes into supercritical gas in the charging zone. Thus, applications for high-pressure spray extraction open up in the domain of pharmaceutical and dietetic products.

BRIEF DESCRIPTION OF THE DRAWINGS

The invention is described in what follows with reference to the drawings.

FIG. 8 shows a charging profile for the fluid in a tubular charging zone.

DESCRIPTION OF THE PREFERRED EMBODIMENTS

Removing the oil from lecithin

Figure 1:
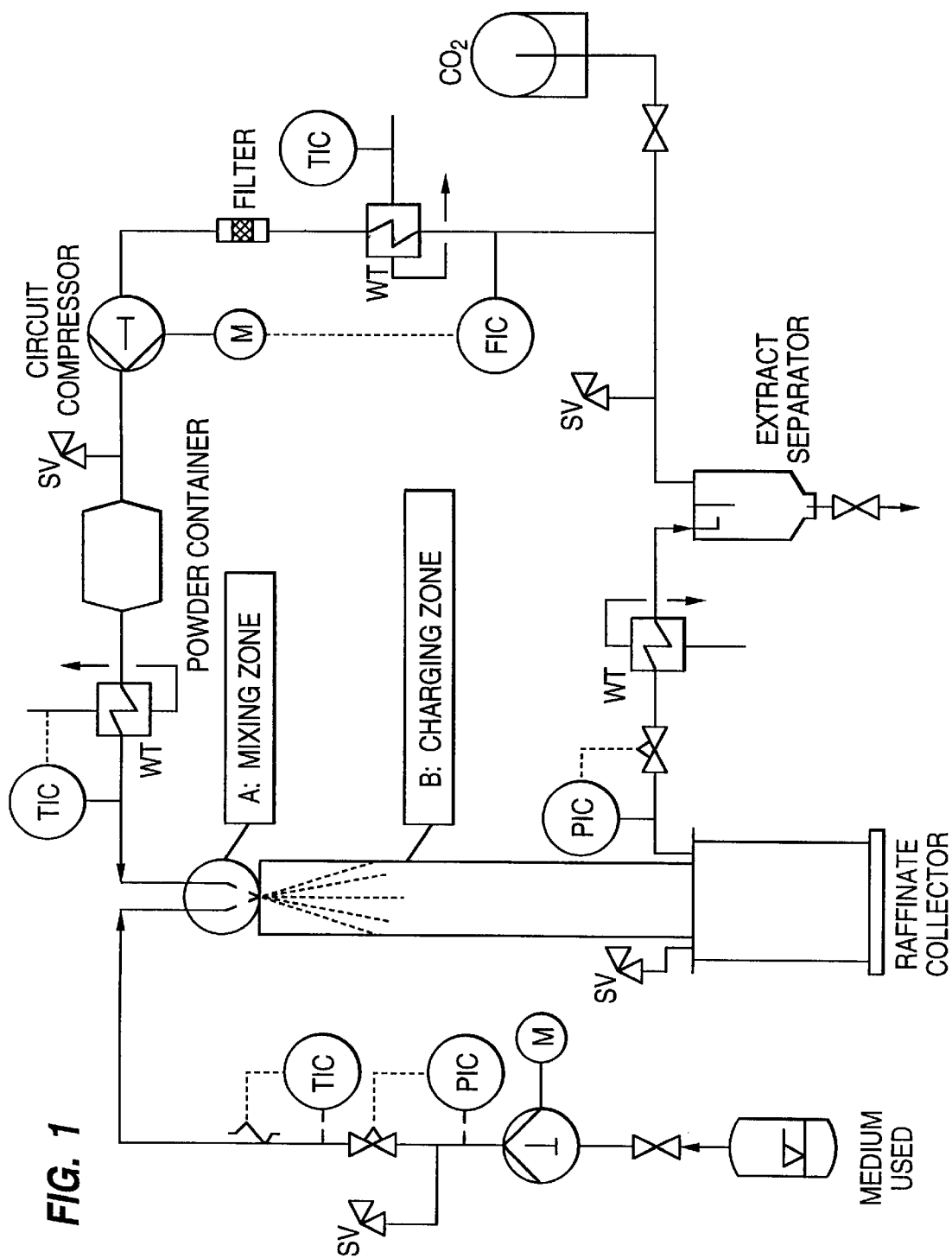
FIG. 1 shows a flow chart of the system for executing the process according to the invention.

Crude soybean lecithin is mixed in a process according to FIG. 1 as medium in the inner mixing chamber of a two-substance nozzle with a supercritical fluid under extraction conditions in the cross-flow and is then sprayed as drop dispersion into a cylindrical charging zone (14.3 mm inside diameter). In the two-phase flow, with dwell times of 20s to 40s, the fluid phase absorbs so much oil from the crude lecithin particles that they are almost completely oilfree. The deoiled lecithin is separated mechanically (cyclone) from the fluid stream and becomes available as valuable substance in powder form in the raffinate collector, while the charged fluid is regenerated in an extract separation stage at reduced pressure levels and temperatures. By compression in a pump and temperature setting in a heat exchanger, the regenerated fluid can be fed again to the mixing zone in the circuit.

When using carbon dioxide as fluid phase, the following process parameters are set:

Extraction pressure: 350 bar–1000 bar (preferably: 450 bar–700 bar)

Extraction temperature: 60° C.–150° C. (preferably: 100° C.–140° C.)

Mass flow ratio (kg fluid/kg medium): 25–100 (preferably 50–75)

Separating pressure: 50 bar–200 bar (preferably: 100 bar–150 bar)

Separating temperature: 20° C.–80° C. (preferably: 40° C.–60° C.).

A crude soybean lecithin with an approx. 65% phosphatide content can be deoiled to a residual oil content of less than 1.5 percent by weight under the preferred conditions.

Very high turbulence is achieved in the mixing zone with Reynolds numbers of 100,000–200,000. A turbulent two-phase flow is preferably also set in the adjacent charging zone with Reynolds numbers of 30,000–50,000.

Crude oil desliming

Crude oil desliming, in which the raffinate resulting from the charged fluid phase as well as the extracted oil form the valuable substances, is carried out under the same extraction and separation conditions as the removal of oil from lecithin. Due to the high 98% oil portion going into the fluid phase, the mass flow ratio must accordingly be raised to 100–300. Although the charging should preferably be carried out in a spherical geometry, a desliming to a phosphorus content of 78 ppm in the oil could already be achieved in a tubular charging zone at 700 bar and 120° C.

Continuous system operation

Until now, no possibility was known to continuously extract from an autoclave a powdered solid as results as raffinate from lecithin deoiling.

Tests have shown that compressed lecithin forms a pressure sealed plug. In this way, an extraction via a pressure-proof extruder with subsequent gas-blocking segment is possible. The lecithin compressed in the extruder forms a pressure-sealed plug in the gas-blocking segment and is extracted as such. This is conceivable particularly when using a self-cleaning twin-shaft extruder, because the transfer is brought to a standstill in a single-shaft extruder due to the cohesion at the screw walls.

For a quasi-continuous operation, the use of two or more extractors operated alternating in batch process and consisting of the atomizing device, the extraction zone and the collector has proven effective. During the emptying of a raffinate collector, the extraction can be continued in another extractor.

Separation of the solid matter transferred

Solid particles are also carried along with the charged oil in the flow from the raffinate collector into the oil separator. This loss of product is attributable to the inadequate separation under gravity due to the small difference in density between the solid matter and the compressed gas. Adequate solid matter retention in the raffinate collector is attainable only in the tangential field. For this, a tangential intake of the two-phase flow is provided in the raffinate collector and, in addition, a high-pressure cyclone is installed downstream under extraction conditions. Only after the high-pressure cyclone is the pressure for the oil separation reduced.

Extraction and separation conditions

The pressures and temperatures in the extraction and separation area should be matched in such a way that energy-saving operation with favorable extraction results can be achieved. In this connection, extraction pressures of 480 bar have proven effective for removing the oil from crude lecithin. At temperatures of 120° C. to 140° C., the density of the extraction gas is lowered with increasing solubility for the valuable substance to be absorbed, in such a way that charging as well as solid matter retention according to 2.4 are effective.

On the other hand, oil separation is to be carried out at pressures as high as possible, so as to reduce the expenditure for recompression of the circuit gas. For this reason, separation conditions under which the gas remains supercritical are suitable. A separating pressure of 150 bar has proven effective at temperatures that set in after tension is released (50° C. to 70° C.). The recompression of the circuit gas can take place under supercritical conditions in such a way that due to the compression heat, the extraction temperature is attained. In this way, the cooling for liquefaction of the gas before recompression as well as the heating after recompression can be saved.

Atomization of the material used

In a known process (EP 0 137 214), the material used is combined with the extraction gas stream in a nozzle-like mixer. This mixer should be replaced by a genuine atomization. The purpose of the atomization is to generate small drops which are extracted in a separate extraction zone with short diffusion paths.

For the materials used, there is the possibility of a viscosity reduction before atomization. For highly viscous natural substances (e.g. crude lecithin), this can be achieved by preheating to a maximum of 70° C. and premixing with a partial stream of extraction gas. The viscosity can be reduced by 10 times by premixing. A continuous premixing of the material used is achieved in a static mixer covered with a pressure tube.

Disintegration of the drops of a highly viscous liquid in the gas stream is achieved only inadequately by the guiding, proposed in the above-mentioned patent, of the extraction gas "in the same direction" as the mixture. For the technical execution, a nozzle form should be chosen in which the extraction gas stream shatters the material stream crosswise to its entry. In this way, the flow pulse of the extraction gas can be used completely for forming drops. The two-phase mixture is formed in an inner mixing chamber of the nozzle before it is sprayed through a taper into the extraction zone.

In addition to such a cross-flow nozzle, a swirling nozzle is also conceivable, in which the gas stream is guided in a swirling flow. A swirling flow cannot be impressed on a highly viscous material, so the material enters the swirling stream of the extraction medium crosswise to it, is reduced in size in so doing, and the drops formed are carried along in the swirling stream as a mixed flow. Then the spraying into the extraction zone also takes place.

Extraction zone

The extraction zone should be designed as an autonomous system component downstream from the atomization. The turbulence and the dwell time of the two-phase flow between the particles formed in the atomization and the extraction gas are regulated in the extraction zone.

In principle, the extraction zone may be designed as a pipe section or as a container. The pipe section is suitable for media that develop a pourable solid immediately after emerging from the atomization (e.g. lecithin). Media that form liquid drops (e.g. crude soybean oil) or form a solid only after an extraction period of finite length must be sprayed into a container with larger diameter (ideal: spherical container), because these media would develop a liquid film on the wall of a pipe section and the surface enlargement obtained during atomization would be eliminated.

The two-phase flow from the extraction zone is guided directly into a raffinate collector in which the raffinate can settle.

Figure 2:
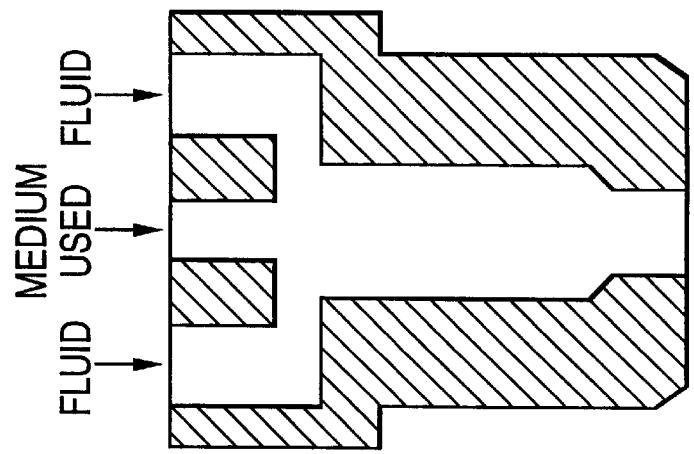

With reference to the drawings the following details are provided:

FIG. 2 shows an embodiment of the mixing zone as a two-substance nozzle with cross-flow guiding and inner mixing chamber.

Figure 3:
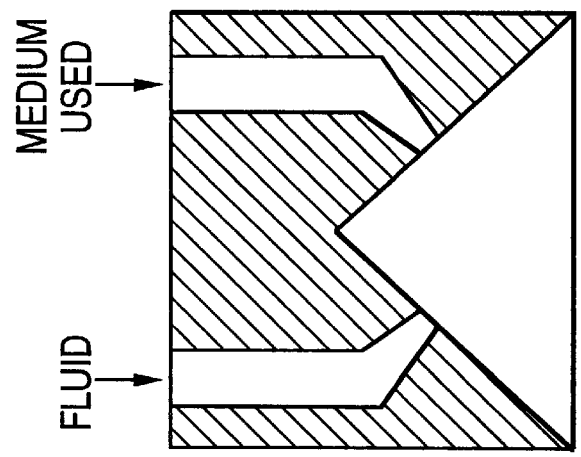

FIG. 3 shows the outer mixing in the impact stream of two single-substance nozzles that are being fed by the fluid and the medium used.

Figure 4:
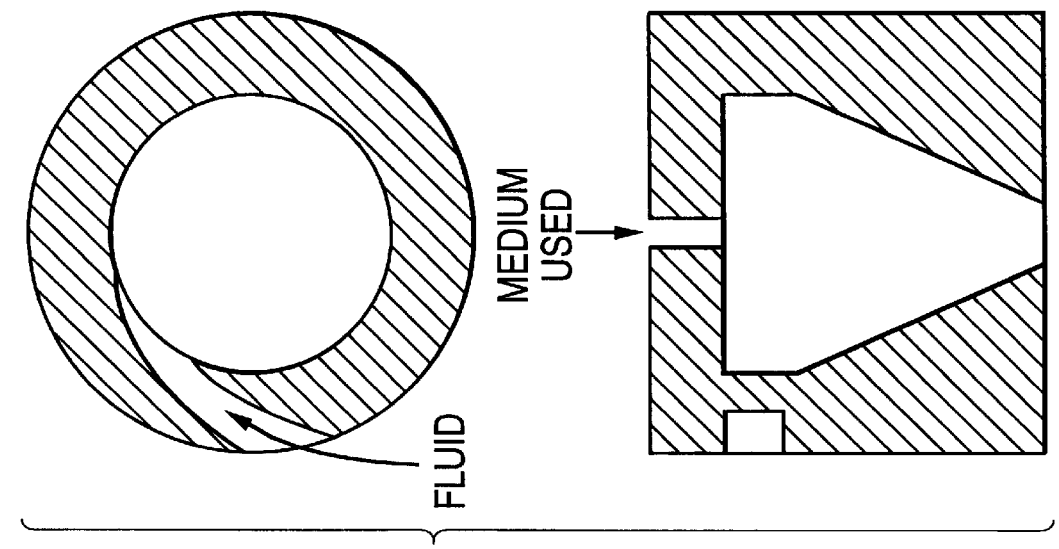
FIGS. 2–4 show schematic embodiments of the mixing zone.

FIG. 4 shows cross section views and longitudinal section views of the development of a swirling nozzle, and the fluid may essentially be fed tangentially and the medium used may essentially be fed axially.

Figure 7:
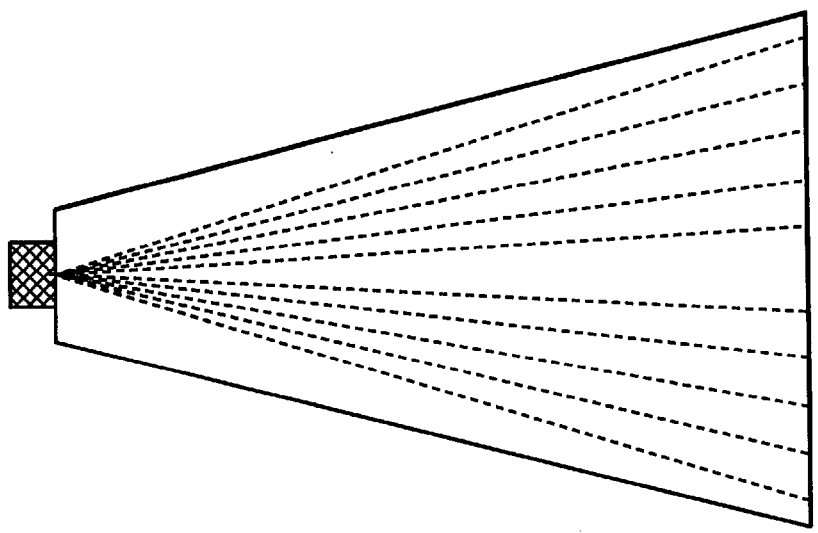
FIGS. 5–7 show schematic embodiments of the charging zone.
Figure 6:
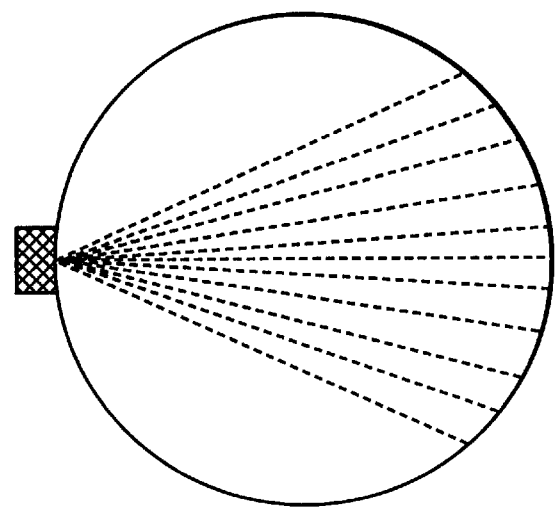
Figure 5:
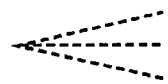
Figure 5:
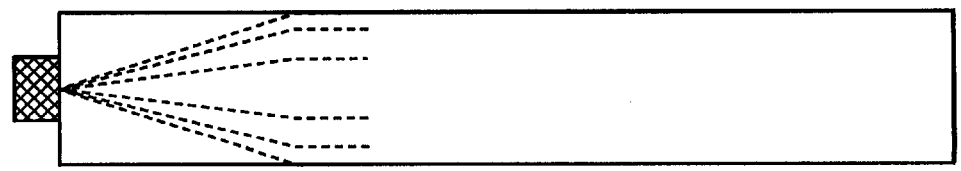

In FIG. 7 the charging zone is shown as a blunt cone 7.

An illustration of the changing profile of the fluid in the tubular charging zone is shown in FIG. 8, with the relative fluid charging being shown along the length of the charging zone. The individual parameters are detailed in the illustration. The mixing zone is indicated as A and the charging zone is indicated as B/C.

We claim:

1. A process for high-pressure extraction of media from liquid solutions and suspensions in the pressure range up to 1,000 bar by means of compressed gases, involving liquid and gas mixing and mass transfer, comprising:

mixing in a mixing zone a flow of a compressed gas with a flow of a liquid containing a medium to form a spray containing spray particles comprising the liquid, the medium and the gas;

directing the spray particles from the mixing zone to a charging and extraction zone spatially separated from the mixing zone;

providing an adequate dwell time of the spray particles in the charging and extraction zone to enable mass transfer to occur; and geometrically optimizing flight trajectories of the spray particles for the purpose of mass transfer in the spray particles.

2. The process of claim 1, wherein the steps of providing adequate dwell time and optimizing flight trajectories comprise, where the mass transfer of the media is complete immediately after the mixing, providing the charging and extraction zone with a first cross sectional area sufficient for complete mass transfer of the spray particles during flight and, where the mass transfer of the media is complete only after an extraction period of finite length, providing the mixing and extraction zone with a second cross sectional area sufficient for complete mass transfer of the spray particles during flight, said second cross sectional area being larger than said first cross sectional area.

3. The process of claim 1, wherein the steps of providing adequate dwell time and optimizing flight trajectories comprise, where the mass transfer of the media is complete immediately after the mixing, providing the charging and extraction zone with a cylindrical shape for complete mass transfer of the spray particles during flight and, where the mass transfer of the media is complete only after an extraction period of finite length, providing the charging and extraction zone with a shape in which the cross sectional area increases with increasing distance from the entry of the sprayed particles into the charging and extraction zone for complete mass transfer of the spray particles during flight.

4. The process of claim 3, wherein the steps of providing adequate dwell time and optimizing flight trajectories comprise providing the charging and extraction zone with one of a spherical shape and a frustoconical shape for media for which the mass transfer is complete only after an extraction period of finite length.

5. The process of claim 1, wherein the compressed gases comprise a member selected from the group consisting of $CO_2$, propane, butane, and mixtures thereof.

6. The process of claim 1, wherein entrainer additives are added to the compressed gases.

7. The process of claim 6, wherein the entrainer additives comprise a member selected from the group consisting of ethanol, propanol, methanol, acetone, water, and methyl-ethyl-ketone.

* * * * *